United States Patent [19]
Ellis

[11] 4,034,787
[45] July 12, 1977

[54] HOT WATER BOTTLE WITH EAR WARMING PROJECTIONS

[76] Inventor: Eugene Ellis, 202 Coast Blvd., La Jolla, Calif. 92037

[21] Appl. No.: 621,222

[22] Filed: Oct. 9, 1975

[51] Int. Cl.² ............................................. A61F 7/12
[52] U.S. Cl. ................................. 150/2.1; 128/380
[58] Field of Search ............ 150/2.1, 2.3; 128/380, 128/402, 403, 400

[56] References Cited

U.S. PATENT DOCUMENTS

| | | | |
|---|---|---|---|
| 677,489 | 7/1901 | Woods | 150/2.1 |
| 768,944 | 8/1904 | Kepler | 150/2.1 |
| 915,824 | 3/1909 | Branaman | 128/380 |
| 1,726,761 | 9/1929 | Palmer | 150/2.1 |
| 2,171,730 | 9/1939 | Lahl | 150/2.1 |

Primary Examiner—Herbert F. Ross
Attorney, Agent, or Firm—Ralph S. Branscomb

[57] ABSTRACT

The invention comprises a hot water bottle having one or more projections extending therefrom which may be provided in different sizes so that the bottle may be used to warm the outer ear cavity to ease the pain of earaches.

2 Claims, 4 Drawing Figures

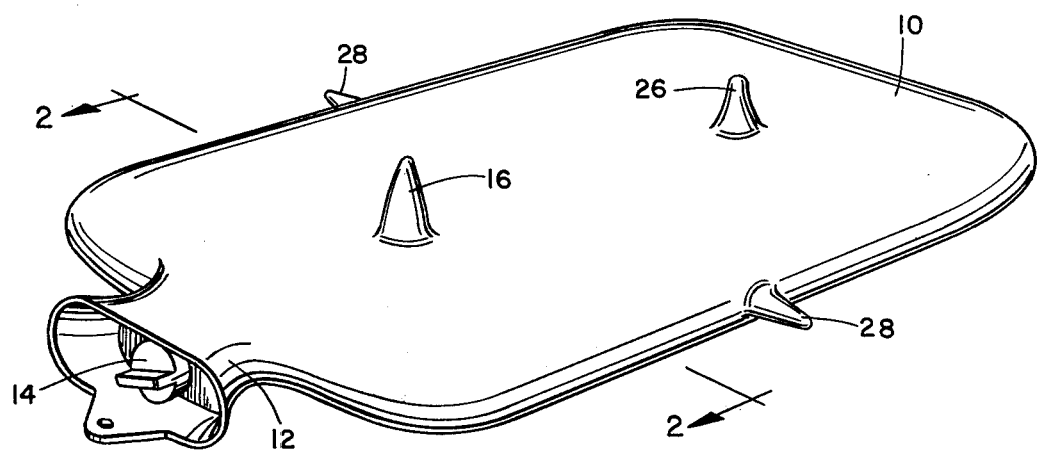
Fig. 1
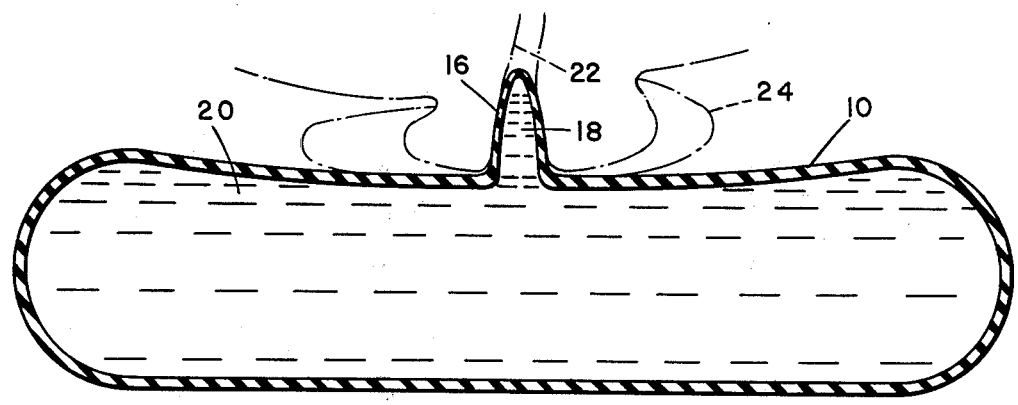
Fig. 2
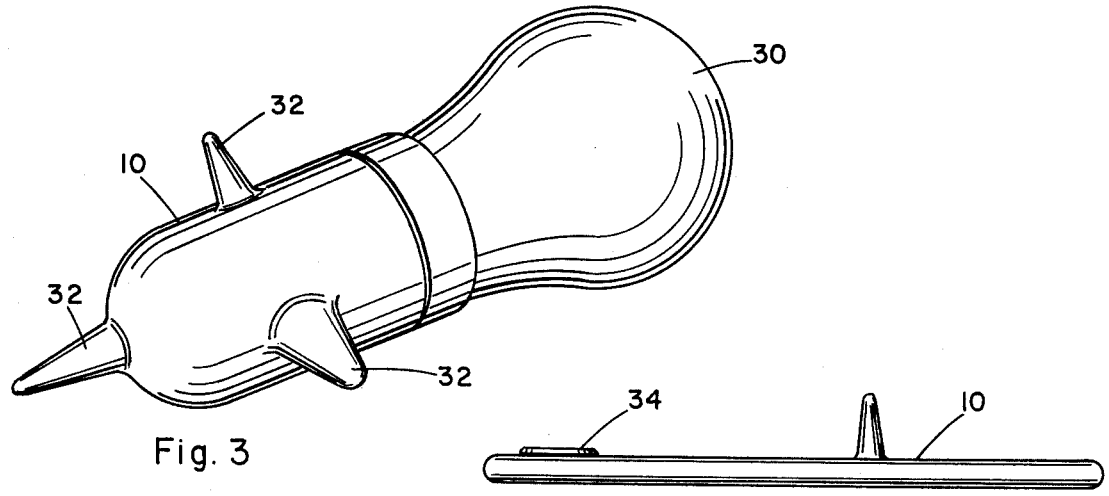
Fig. 3
Fig. 4

HOT WATER BOTTLE WITH EAR WARMING PROJECTIONS

BACKGROUND OF THE INVENTION

The invention relates to hot water bottles or bags commonly used to ease cramps and aches and for other applications in which it is desirable to apply dry heat to the body. The common shape of these bottles is generally flat with a slightly squared plan form so that a maximum area of the body can be brought in contact with the heat emanating from the warm water contained in the bag. Although this configuration has been altered for particular uses and to adapt the bag contours to different specific areas of the human body, no hot water bag has been developed which is suitable for use in warming the ear, including the outer ear cavity, to assuage the pain produced by an earache.

SUMMARY OF THE INVENTION

The hot water bottle of the present invention is an improvement over present art and is designed particularly to conform to the shape of the ear to provide soothing heat both to the ear itself, including the ear cavity, and in some embodiments the entire side of the head as well. The structure is functionally similar to a conventional water bottle but contains additionally one or more nipple-like projections dimensioned to fit within the ear to provide heat directly to the ear cavity. The water compartment portion of the bottle may be shaped much as a conventional unit with a projection extending from the flat side area, or diminished in size and somewhat bulb shaped with a knob-like handle for convenient use by a person in a sedentary or other non-prostrate position.

BRIEF DESCRIPTION OF THE DRAWINGS

FIG. 1 is a perspective view of a hot water bottle incorporating several ear plug projections;

FIG. 2 is an enlarged sectional view taken on line 2—2 of FIG. 1, illustrating the use of the bottle;

FIG. 3 is a perspective view of a hand held hot water container with ear plug projections; and FIG. 4 is a side elevation view of a thin flat form of bottle.

DETAILED DESCRIPTION OF THE PREFERRED EMBODIMENT

The basic form of the invention is shown in FIG. 1 in which a water container 10 is used which is similar to those of conventional hot water bottles or bags. The container 10 is ordinarily composed of a flexible rubbery material and has a flared mouth 12 which shields a rubber stopper 14 which is ordinarily screwed into a water filler inlet, not shown, through which the container is charged with warm water for use.

The container 10 is provided with a projection 16 which is somewhat centrally located, or at least inwardly disposed from the edges of the container so that a generally planar expanse of the bag surrounds the projection. As shown in FIG. 2, the projection is preferably hollow as at 18 so that warm water, indicated at 20, may circulate through the bag and into the interior hollow of the projection. The projection is dimensioned to be comfortably received in the cavity 22 of the ear 24, again as shown in FIG. 2, and the flat areas surrounding the projection warm the extended part of the ear as well as the portion of the head surrounding the ear so that the entire area is soothed with heat to ease the pain of an earache which may or may not be entirely localized within the ear cavity.

Referring to FIG. 1, a second projection 26 is illustrated in approximately the same position as the projection 16 but at the other end of the bag. This projection may be of a different size or shape than the first mentioned projection to accomodate ears which may be too large or small to receive the projection 16, and other projections may be provided on the other side or in other locations of the container such as those shown at 28, both for the purpose of providing a greater variety in size and shape and to include projections at different locations on the container so that different orientations of the bottle reletive to the head of the user may be achieved to satisfy individual preferences.

FIG. 3 discloses a slight modification of the invention in which the container portion 10 is small and generally bulb shaped and is attached to a knob 30 which is small enough to be conveniently held in the hand. The water container and knob may be separable so that the knob in effect forms the plug of the water bottle, and whereas the previously mentioned embodiment would be fairly convenient to use against a pillow with the user's head placed thereon, the modification illustrated in FIG. 3 would be most convenient when the victim is in a sitting or standing position and the bulk of the larger bag would interfere with other activities. The projections 32 in this smaller version can clearly be seen to vary slightly both in length and in the conical angle assumed to accomodate a variety of persons, having ear cavities of different configurations.

FIG. 4 illustrates an embodiment very similar to that shown in FIGS. 1 and 2 but the container 10 has been flattened so that it may be more easily used in extended position on a pillow or bed when the user is in an inclined position. Due to its flattened shape, this water bottle may have a differently shaped and positioned plug 34 to seal the water inlet.

The hot water bottle described herein can be manufactured simply and at a cost comparable to that of conventional models, and, with reference especially to the embodiment in FIG. 4, can be used for other areas of the body other than the ear and in conventional fashion.

I claim:

1. A hot water bottle to heat the human outer ear cavity comprising:
   a. a flexible watertight container being generally smooth in external contour and substantially flattened to define two generally planer sides;
   b. at least one generally conical projection shaped to substantially fill the outer human ear cavity and extending generally centrally and unobstructedly from one of said sides whereby said hot water bottle is conveniently useable on a horizontal surface;
   c. said projection being at least in part hollow and internally communicating with said container to receive the circulation of hot water within said container; and
   d. means to completely fill said container and projection with hot water.

2. A hot water bottle to heat the human outer ear cavity comprising:
   a. a flexible watertight container being generally smooth in external container;

b. said container being provided with a separable hollow dimensioned to be hand-held, said container and said knob being of similar size;
c. said container being provided with a plurality of generally conical projections, said projections being at least in part hollow and internally communicating with said container to receive the circulation of hot water therein;
d. said hollow projections being of different sizes and shaped to substantially fill the outer human ear cavity of various sized outer ear cavities; and
e. means to completely fill said container, knob and projections with hot water.

* * * * *